United States Patent [19]

Stiehl et al.

[11] Patent Number: 5,496,286
[45] Date of Patent: Mar. 5, 1996

[54] HYPODERMIC SYRINGE HOLDER WITH DISPOSABLE BODY

[75] Inventors: Mark A. Stiehl, Rochester; William A. Bergstresser, Prattsburgh; George E. Diaz, Rochester, all of N.Y.

[73] Assignee: Sterling Winthrop, New York, N.Y.

[21] Appl. No.: 292,118

[22] Filed: Aug. 17, 1994

[51] Int. Cl.$^6$ .................................................. A61M 5/00
[52] U.S. Cl. .................................................. 604/232
[58] Field of Search .................................. 604/232, 233, 604/234, 235, 187, 218, 228

[56] References Cited

U.S. PATENT DOCUMENTS

| | | | |
|---|---|---|---|
| 3,026,873 | 3/1962 | Miskel et al. | 604/232 |
| 4,931,040 | 6/1990 | Haber et al. | 604/232 X |
| 5,078,698 | 1/1992 | Stiehl et al. | |
| 5,350,367 | 9/1994 | Stiehl et al. | 604/232 |

FOREIGN PATENT DOCUMENTS 0485028  10/1991  European Pat. Off. .

*Primary Examiner*—John D. Yasko
*Attorney, Agent, or Firm*—William J. Davis; Paul E. Dupont

[57] ABSTRACT

A hypodermic syringe holder adapted to receive a disposable ampoule and eject it in an axial direction. The holder comprises a plunger element, a holding element and a disposable hollow cylindrical frame portion.

4 Claims, 5 Drawing Sheets

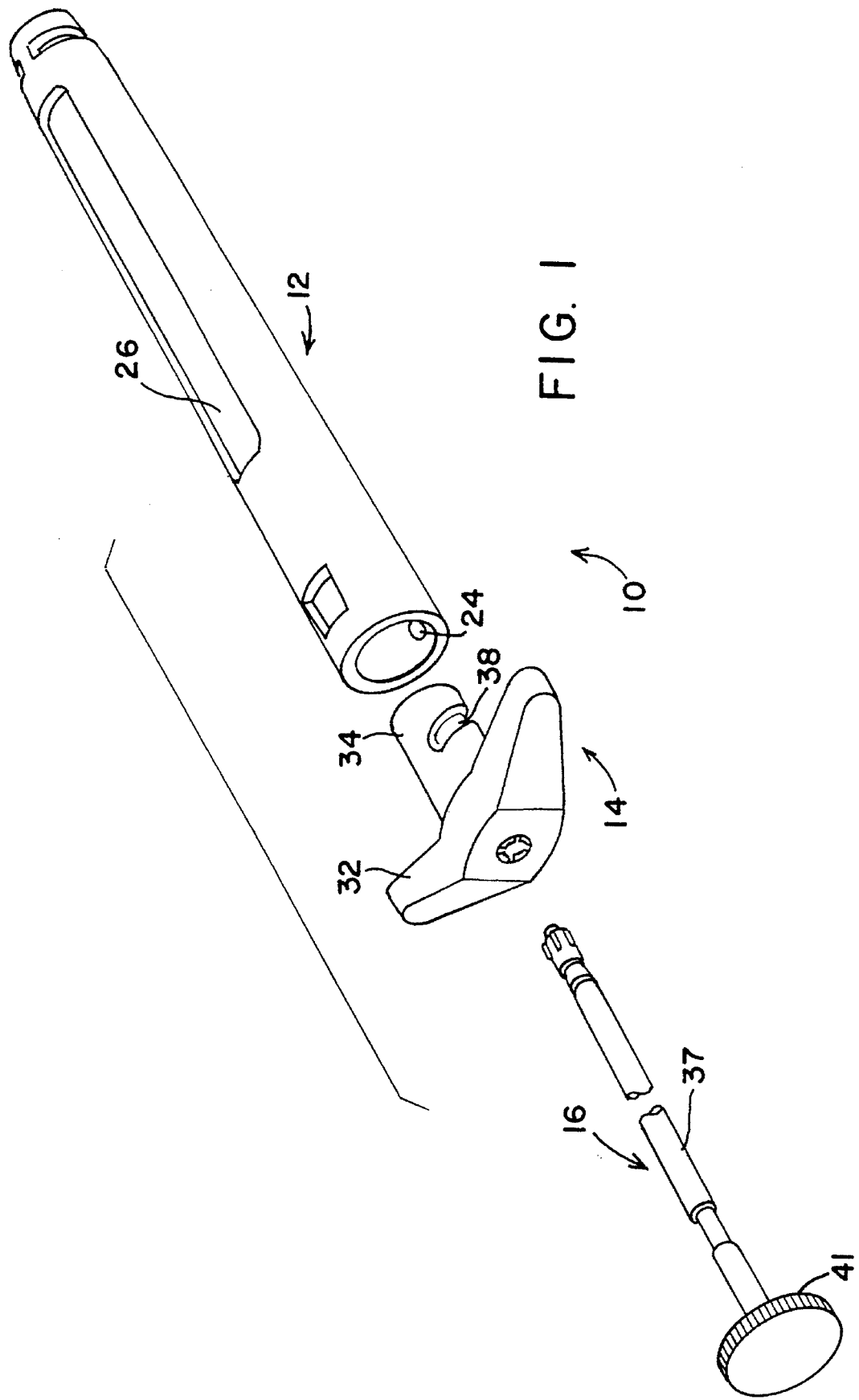

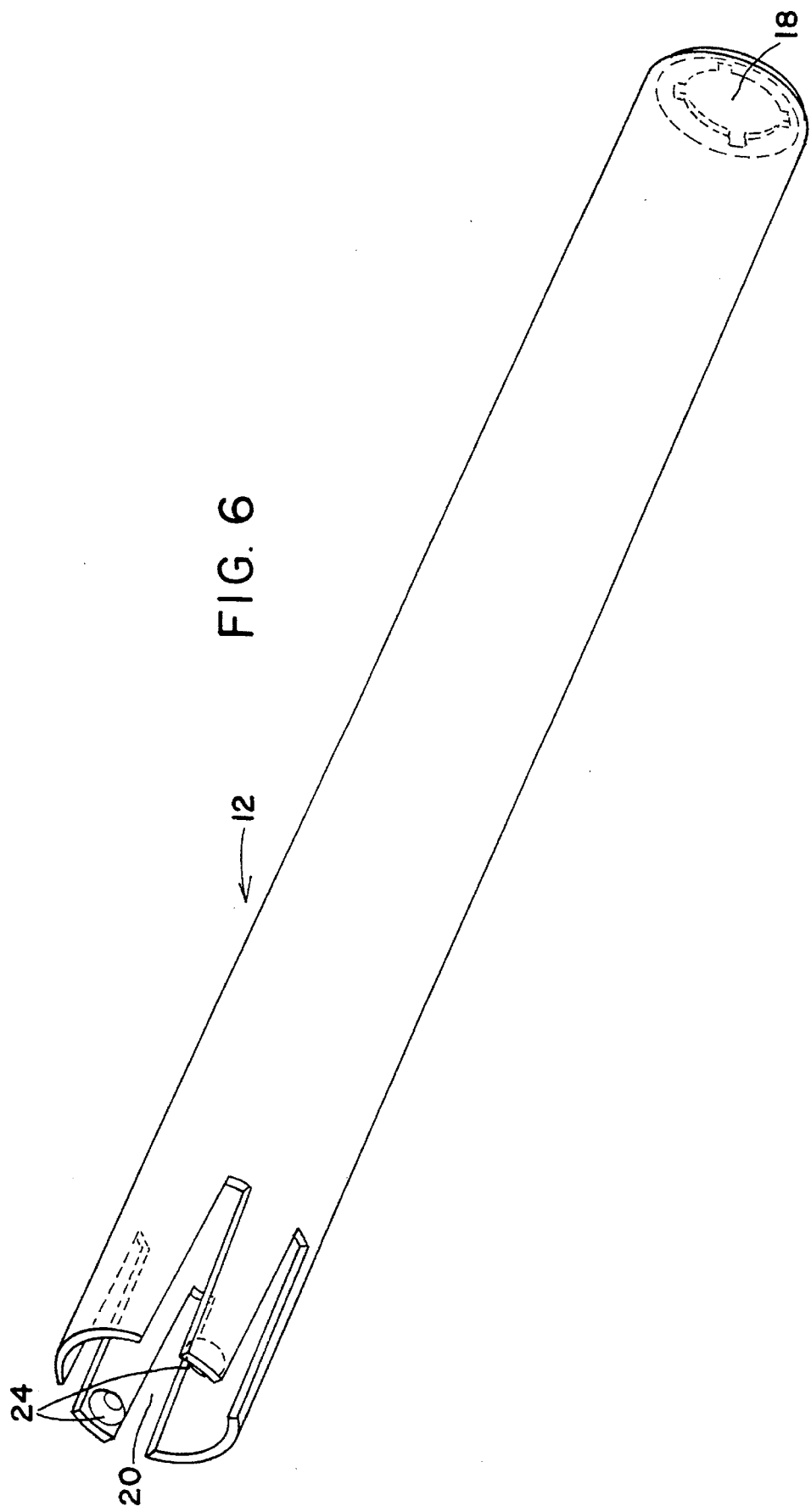

HYPODERMIC SYRINGE HOLDER WITH DISPOSABLE BODY

BACKGROUND OF THE INVENTION

1. Field of the Invention

This invention relates to the field of hypodermic syringe holders for use in combination with disposable medicament-containing ampoules.

2. Description of the Prior Art

Disposable medicament-containing cartridge-needle units for use in conjunction with hypodermic syringe holders are well known in the art. Such cartridges conventionally feature a cylindrical body closed at the proximal end with a flexible piston slidable within the bore of the cartridge and closed at the distal necked-down end with a diaphragm secured to the cartridge by a crimped-on metal collar. The necked-down distal end conventionally is fitted with a steel needle/needle hub unit and a needle sheath. Such needle/needle hub units have, minimally, a sharp end, typical of the type associated with hypodermic syringes.

Such cartridge-needle units can be used in conjunction with syringe holders which allow the user to avoid handling the cartridge-needle unit when the needle is exposed. Nevertheless, health care workers are especially susceptible to accidental and potentially infectious, and indeed, on occasion, possibly fatal, needle strikes due to careless handling and/or disposal of the cartridge-needle unit after use. The consequences to health care workers of strikes from needles contaminated with various infectious diseases such as hepatitis or AIDS can be particularly severe. The frequency of such accidental needle strikes in the United States is surprisingly great, and has been estimated to be approximately one million needle strikes per year. However, the cost to health care organizations for the testing of health care workers accidentally stricken by used needles is a significant burden on health care costs. Therefore, it would be desirable to further protect health care workers by providing medicament-containing cartridges without having to expose the user to the needle commonly associated with such cartridges.

In response to the "accidental needle strike" situation, numerous devices have been developed which allow the spent disposable medicament-containing ampoules to be removed from the holder without handling by the health care worker.

EPO case 0485028A1 describes a readily assemble, snap together hypodermic syringe holder. The body of the holder is a semi-cylindrical body. When the ampoule is to be ejected, the semi-cylindrical is positioned so its open side is faced downward. Gravity forces permit the ampoule to fall. The problem with this holder is that occasionally the ampoule is caught, thereby altering the trajectory of the ampoule's fall. This altering of the trajectory may cause "accidental needle strikes" or at the very least may cause broken glass, potentially contaminated, on the floor.

U.S. Pat. No. 5,078,698 describes an axial eject hypodermic syringe holder. This holder has a pair of pivotable jaws at the needle end of the holder. When the medicament-containing ampoule is to be removed from the holder and dropped by gravity into a disposal unit, the jaws are opened sufficiently to allow the ampoule to slidingly eject from the holder. The problem with this holder is the amount of parts required and the overall size of "bulk" of the holder. Additionally, multiple layers of plastic may negatively effect cartridge visibility.

It would be highly desirable to provide a holder having a simplified and improved construction which allows for axial ejection of the ampoules.

SUMMARY OF THE INVENTION

In accordance with this invention, there is provided an improvement in a hypodermic syringe holder adapted to receive a disposable ampoule comprising:
  (a) a frame portion shaped to receive an ampoule,
  (b) a plunger element having a rod, and
  (c) a holding element,
wherein the improvement is that the frame portion:
  (a) is a disposable hollow cylinder,
  (b) is adapted to receive the disposable ampoule through an opening at its proximal end,
  (c) has at least one projecting lug on the inside surface of its head portion, wherein at least one lug positions and frictionally fits with the holding element, and
  (d) at the lower end has a slot sized to fit around the ampoule's needle hub and to position the ampoule.

In another embodiment this invention, there is provided an improvement in a hypodermic syringe holder adapted to receive a disposable ampoule comprising:
  (a) a frame portion shaped to receive an ampoule,
  (b) a plunger element having a rod, and
  (c) a holding element,
wherein the improvement is that the frame portion:
  (a) is a disposable hollow cylinder,
  (b) is adapted to receive the disposable ampoule through an opening at its proximal end,
  (c) has a projecting lug on the inside surface of the head portion, wherein the lug positions frictionally fit with the holding element,
  (d) has raised ribs located near the upper and lower end, respectively, of the frame portion to align the ampoule,
  (e) has a viewing window, and
  (f) at the lower end has a slot sized to fit around the ampoule's needle hub.

In accordance with a prefilled embodiment with this invention, there is provided a hypodermic syringe holder adapted to receive a disposable ampoule comprising:

a disposable cylindrical body or frame portion having a generally cylindrical head portion, the head portion having on its inside surface a projecting lug;

an axially movable holding element rotatable about its longitudinal axis within the cylindrical head of the body portion and engageable with the rim of an associated ampoule to securely immobilize the ampoule within the body portion of the syringe holder, the holding element comprising a barrel portion, a handle portion, a helical groove on the outer surface of the barrel portion, a bore therethrough and ramp means connecting the helical groove with the lower surface of the holding element, the barrel portion being sized to rotate and translate within the cylindrical head;

a plunger element including a rod portion having on its lower end a piston engaging means, the rod portion and piston engaging means being axially and slidably receivable within the bore of the holding element;

wherein the helical groove is slidably accessible to the lug through the ramp means and engageable with the lug, whereby the lug secures the holding element to the body portion such that all of the elements of the syringe holder are in cooperative engagement with one another.

It is an advantageous feature of this invention that there is provided a syringe holder of simple construction, i.e., containing just three working parts, which can be easily and economically manufactured in large quantities, e.g., by injection molding techniques.

It is another advantageous feature of this invention that there is provided a syringe holder which can be readily assembled, i.e., by snapping together the body portion, holding element and plunger element.

Yet another advantageous feature of this invention is that there is provided a syringe holder readily adapted to immobilize a cartridge ampoule within the holder during use having manual aspirating capability.

Other advantages will become readily apparent upon reference to the following description of preferred embodiments when read in light of the accompanying drawings.

BRIEF DESCRIPTION OF THE DRAWINGS

FIGS. 1 through 4B relate to a preferred embodiment of the invention.

FIG. 1 is an exploded perspective view of a preferred syringe holder of the invention;

FIGS. 4A and 4B are plan and end views, respectively, of a plunger element of a syringe holder of the invention.

FIGS. 5 and 6 relate to another embodiment of the invention.

FIG. 5 is a perspective view of a holding element with a plunger element operationally inserted therein.

FIG. 6 is a perspective view of a disposable frame portion.

DESCRIPTION OF PREFERRED EMBODIMENTS

While this invention is described particularly with respect to a hypodermic syringe holder, it also finds utility in other holders adapted to dispense a fluid from a disposable cartridge.

As used herein, the terms "lower" and "downward" are intended to make reference to the needle (distal) end of the syringe holder and associated parts. Conversely, the terms "upper" and "upward" are intended to make reference to the proximal end of the holder.

Referring to FIG. 1, a preferred syringe holder of the invention, represented by 10, is intended for use in combination with conventional medicament-containing ampoules, not illustrated herein, which are closed at the upper end with a flexible piston slidable within the bore of the ampoule and closed at the lower necked-down end by a rubber diaphragm secured to the ampoule by a crimped-on metal collar. The necked-down end is conventionally fitted with a needle/needle hub unit and a needle sheath. A typical such ampoule/needle assembly is sold commercially as CARPUJECT®.

In preferred embodiments, the syringe holder comprises a total of three elements, namely, a generally semi-cylindrical body or hollow frame portion 12, a holding element 14, and a plunger element 16.

Figure 2A:
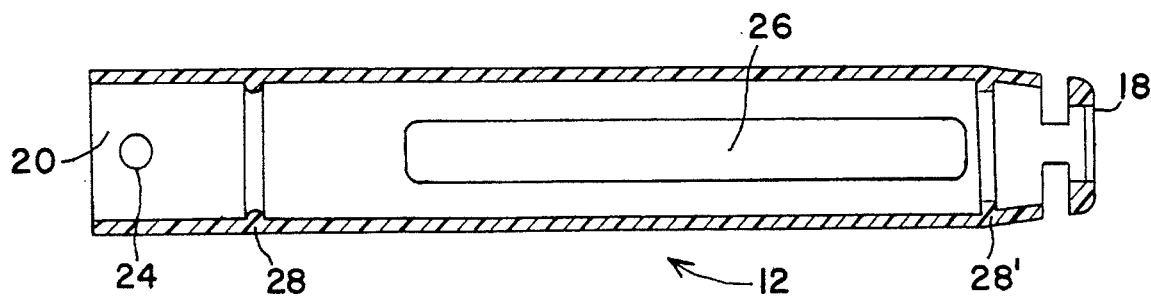
FIGS. 2A and 2B are a cross-sectional plan view and a cross-sectional side elevational view partially in section, respectively, of a disposable frame portion of a syringe holder of the invention.
Figure 2B:
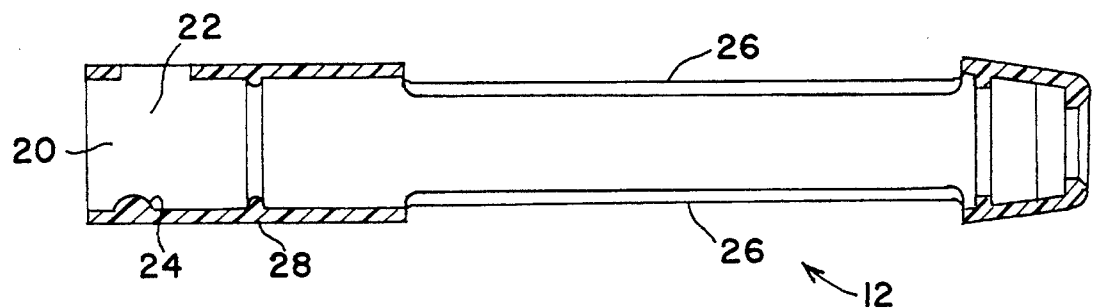

With reference to FIGS. 2A and 2B, the disposable body portion comprises a generally cylindrical hollow unit which is adopted for loading an ampoule through the proximal end of the body.

The lower end of the body has a slot 18, sized to fit around the needle hub of an ampoule/needle/needle hub/needle sheath unit used in combination with the holder.

The upper end (head) of the body is sized to permit the ampoule to be placed into the body through an opening 20. The opening 20 also receives the holding element 14.

The head portion of the body is provided on its inside surface with a lug 24 the purpose of which is described in further detail herein below.

The lug is preferably hemispherical and can conveniently be molded integrally with the body, thus eliminating the need for additional molding and sealing of the lug or a boss element to the body.

The holder may also have viewing windows 26, which are particularly desirable when the syringe holder is used as an aspirating syringe and the body is fabricated of a material which does not exhibit good transparency. The body portion optionally can be equipped with raised ribs 28 or 28' located near the upper or lower end, respectively, of the body portion, which aid to align an ampoule within the body of the syringe holder with the tip of the piston engaging means 40.

Figure 3A:
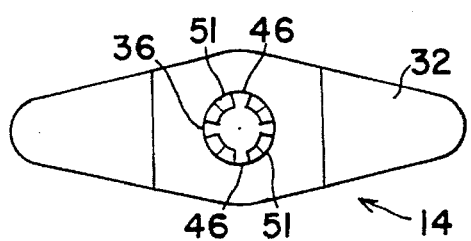
FIGS. 3A, 3B and 3C are an end view, a plan view and a cross-sectional view, respectively, of an holding element of a syringe holder of the invention.
Figure 3B:
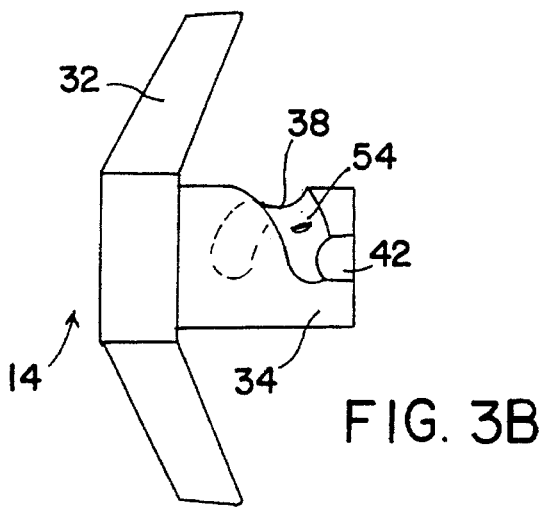
Figure 3C:
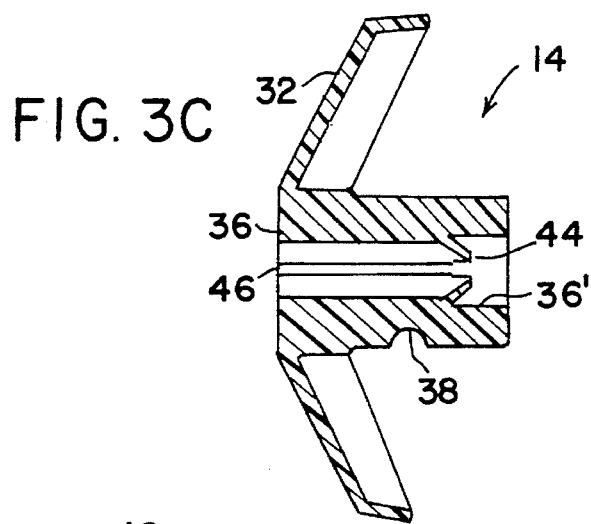
Figure 4A:
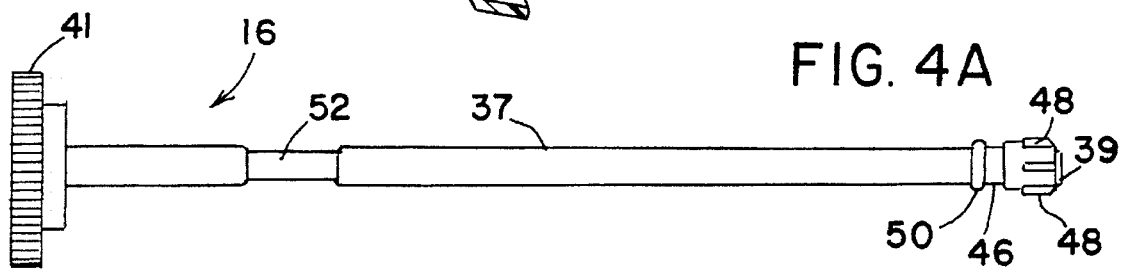
Figure 4B:
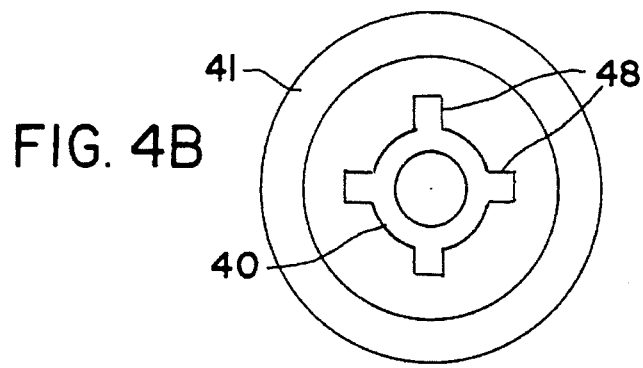

The ampoule holding element shown in FIGS. 3A, 3B and 3C consists of a pair of handles 32 and a barrel 34 having a relatively small diameter bore 36 sized to slidably receive at least the shaft 37, and preferably both the shaft and head portions 39 of plunger element 16 shown in FIGS. 4A and 4B. The barrel of holding element 14 has a slightly expanded bore section 36' which is sized to accept piston engaging means 40 and which has a slightly larger diameter than the shaft portion of the plunger. Extending partially around the outer surface of holding element 14 is a helical groove 38. Helical groove 38 is semi-circular in cross section and is of such width and depth that it will slidably receive hemispherical lug 24 on the inside surface of the proximal portion of body 12 when the holding element is appropriately, i.e. slidably inserted into the body.

The plunger element preferably consists of a unitary injection moldable structure. However, the piston engaging means 40 and/or the actuation button 41 may be affixed to the rod after the rod has been inserted through the bore of the holding element.

The barrel portion of the holding element is provided with ramp means 42 connecting the distal part of helical groove 38 with the distal surface of the holding element. Helical groove 38 is slidably accessible to hemispherical lug 24 through ramp means 42 and engageable with the lug in such a manner so as to secure the holding element to the body portion such that all the elements of the syringe holder are in cooperative engagement with one another.

In particularly preferred embodiments of the invention, holding element 14 is provided with fingers 44 and grooves 46 on the inside diameter of bore 36, the distal portion of rod 37 is provided with fins 48, and the distal portion of rod 37 is provided with undercut means 46'. When inserted through the bore, the fins travel through the grooves and the head of the rod is capable of flexing the fingers. The fingers are engageable with the undercut means to capture the plunger element in the holding element. The fins simulate a larger head diameter engageable with the ampoule which is desirable, while the smaller rod diameter reduces drag for aspiration and minimizes undesirable relaxation of the fingers, for example, that which can result during high temperature sterilization. Keying means 51 can be provided so that the fins align themselves with the grooves upon insertion of the distal portion of the plunger element into the bore. The rod can be provided with radial ribs 50 which retain the plunger rod in the rear position and aid in cartridge ejection, and detent means 52 which functions to minimize undesirable relaxation of the fingers.

As noted above, the various parts of the syringe holder can be readily assembled. For example, plunger element 16 can be inserted through the bore of holding element 14 in a "one way" or "insert only" manner. The resulting holding element/plunger element subassembly can then be inserted into the opening of the proximal end of body portion 12. The holding element is rotated so that the ramp means engages the hemispherical lug on the inside surface of the body portion. The holding element is then pressed into the body such that the hemispherical lug slides through the ramp means and acquires access to the helical groove. All the elements of the syringe holder are thereby joined together in cooperative relationship with one another. It is a particularly advantageous feature of this invention that a syringe holder is provided containing just three working parts which can be easily assembled merely by snapping together the various pieces. This avoids the costly and undesirable step of gluing, mechanically attaching, and/or thermal, sonic or solvent welding the pieces together.

By rotating the holding element approximately one half revolution in one direction or the other, the holding element can move either forward to a fully engaged position or backward to a fully retracted position.

In use, an ampoule/needle/needle hub/needle sheath unit is inserted into the opening 20 of the proximal end of the body. The holding element is then inserted into the opening until the lug 24 via the ramp means 42 is engaged into the helical groove 38.

The holding element is given one half turn in the opposite direction to cause the shoulder of the holding element to bear against the rim of the ampoule, thus securing it firmly in place within the holder. The plunger is then engaged with the piston of the ampoule. One means of achieving such engagement is to turn the plunger rod so as to engage a screw threaded hole in the end of the piston engaging means 40 with a screw-threaded post on the piston. The holding element may optionally be equipped with a pair of raised ribs 54 located near both ends of helical groove 38 which serve to lock the holding element in the fully engaged or fully retracted positions.

Figure 5:
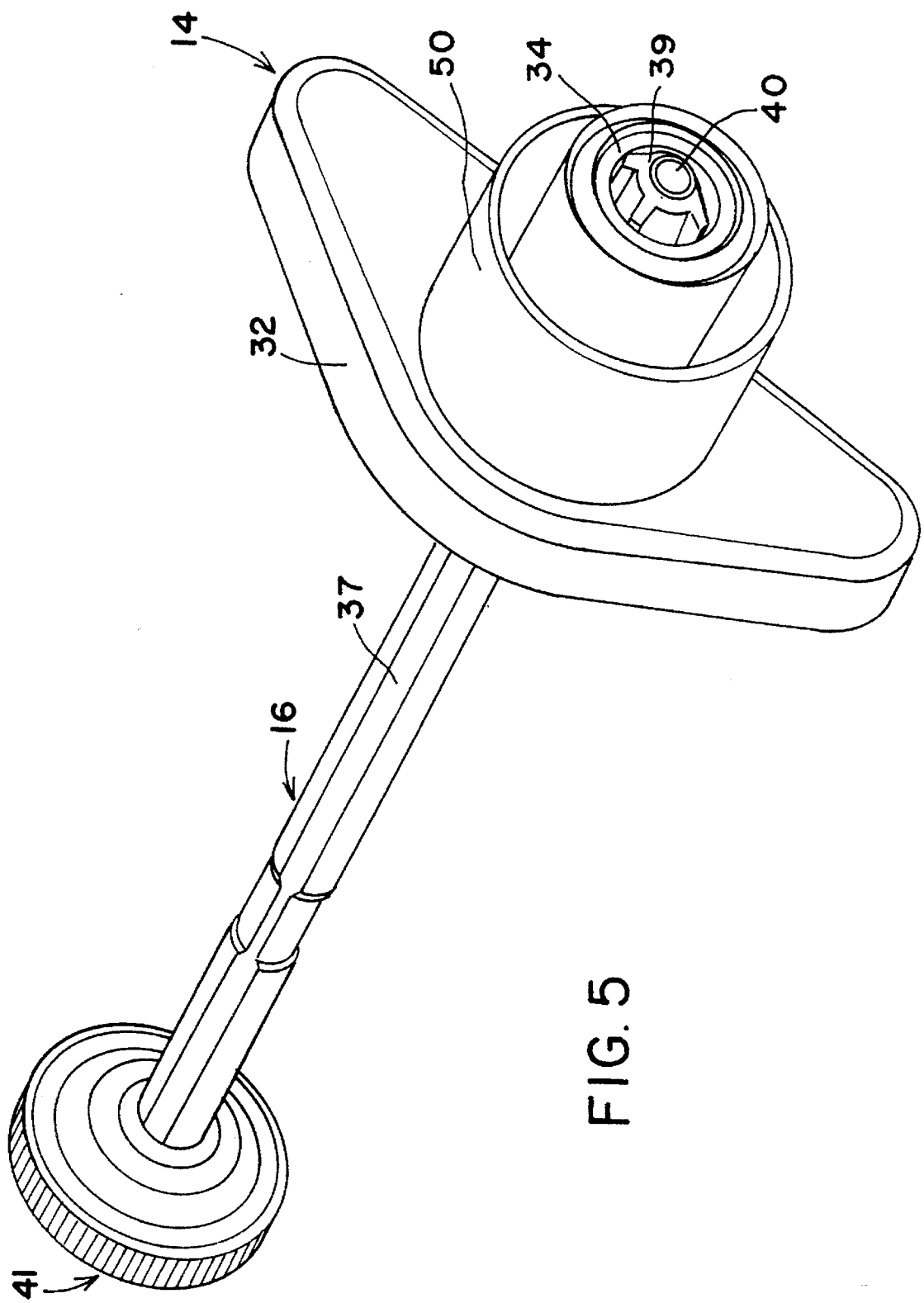

Referring to FIG. 5, plunger element 16 is shown inserted into holder element 32. The plunger has a shaft 37, head 39, piston engaging means 40 and activation button 41.

The holder element 14 has a pair of handles 32 and a barrel 34 having a relatively small bore sized to slidably receive the shaft and head portion of the plunger. The holder also has a surface 50 to which the disposable frame portion shown in FIG. 6, can be removeably attached.

Referring to FIG. 6, the disposable frame portion 12 comprises a generally hollow unit having an opening at the proximal end 20 for loading the ampoule. The opening is also sized to frictionally fit the surface of the holder element.

The head portion of the frame portion is provided on its inside surface with lugs 24 which provide a removable frictional attachment of the frame portion to the holder element.

Although the various elements of the syringe holders described herein may be made of any suitable material including metals or plastics, they are well adapted to fabrication of plastic. In particular, body portion 12, holding element 14 and plunger element 16 can be fabricated by known precision injection molding techniques. When the various elements are constructed of plastic, suitable plastics include high density polypropylene, polycarbonate, polystyrene, ABS (clear of opaque), nylon, acetals such DELRIN® or polyethylene. It is particularly advantageous that the body portion be fabricated of a transparent material so that the ampoule is visible during operation. The plastic preferably is injection moldable. As noted, a particularly advantageous feature of this invention is that the various pieces of the syringe holder, i.e., the body, holding element and plunger element can be easily and economically manufactured in large quantities by known precision injection molding techniques. When the holder is intended for use in a high temperature sterilization process, the plastic preferably is substantially resistant to deformation at sterilization temperatures.

It will be appreciated that minor modifications in the various elements of the invention may be made without departing from the spirit of the invention. For example, the piston engaging means is described herein as being a screw-threaded element which mates with a screw-threaded post on the ampoule piston. Such means of engaging the plunger with the piston is a preferred means, however, other piston engaging means well known in the art, such as, for example, multiple retractable claws or hooks, fixed claws, an expandable chuck, resilient gripping fingers, a harpoon, or a bayonet connection will serve the purpose as well.

We claim:

1. An improvement in a hypodermic syringe holder adapted to receive a disposable ampoule comprising:
    (a) frame portion shaped to receive an ampoule containing a needle hub,
    (b) a plunger element having a rod, and
    (c) a holding element,
wherein the improvement is that the frame portion:
    (a) is a disposable hollow cylinder,
    (b) is adapted to receive the disposable ampoule through an opening at its proximal end,
    (c) has a head portion at the proximal end thereof and at least one projecting lug on the inside surface of the head portion, wherein the lug positions and frictionally fits with the holding element, and
    (d) at the lower end has a slot sized to fit around the ampoule's needle hub and to align the ampoule.

2. An improvement in a hypodermic syringe holder adapted to receive a disposable ampoule comprising:
    (a) frame portion shaped to receive an ampoule containing a needle hub,
    (b) a plunger element having a rod, and
    (c) a holding element,
wherein the improvement is that the frame portion:
    (a) is a disposable hollow cylinder,
    (b) is adapted to receive the disposable ampoule through an opening at its proximal end,
    (c) has a head portion of the proximal end thereof and a projecting lug on the inside surface of the head portion, wherein the lug positions and frictionally fits with the holding element,
    (d) at the lower end has a slot sized to fit around the ampoule's needle hub, (e) has raised ribs located near the upper and lower end, respectively, of the frame portion to align the ampoule, and (f) has a viewing window.

3. A hypodermic syringe holder adapted to receive a disposable ampoule comprising:

(a) a disposable cylindrical hollow frame portion shaped to receive an ampoule and having a generally cylindrical head portion, said head portion having on its inside surface a projecting lug;

(b) an axially movable holding element rotatable about its longitudinal axis within the cylindrical head of said frame portion and engageable with an associated ampoule to securely immobilize the ampoule within the frame portion of the syringe holder, said holding element comprising a barrel portion, a handle portion, a helical groove on the outer surface of said barrel portion, a bore there through, a ramp means for permitting said lug to access said helical groove connecting said helical groove with the distal end surface of said holding element; said barrel portion being sized to rotate and translate within said cylindrical head;

(c) a plunger element having a rod portion on its distal end means for engaging a piston of an associated ampoule, said rod portion and piston engaging means being axially and slidably receivable within said bore of said holding element;

wherein said helical groove is slidably accessible to said lug through said ramp means and engageable with said lug, whereby said lug secures the holding element to said frame portion such that all of the elements of the syringe holder are in cooperative engagement with on another.

4. The syringe holder of claim 1 wherein said frame portion, said holding element and said plunger element are fabricated of plastic.

* * * * *